US011139054B2

(12) United States Patent
Takahashi et al.

(10) Patent No.: US 11,139,054 B2
(45) Date of Patent: Oct. 5, 2021

(54) MEDICAL-INFORMATION PROVIDING SYSTEM AND MEDICAL-INFORMATION PROVIDING METHOD

(71) Applicant: OLYMPUS CORPORATION, Tokyo (JP)

(72) Inventors: Keigo Takahashi, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 25 days.

(21) Appl. No.: 16/223,200

(22) Filed: Dec. 18, 2018

(65) Prior Publication Data

US 2019/0131005 A1     May 2, 2019

Related U.S. Application Data

(63) Continuation of application No. PCT/JP2016/069453, filed on Jun. 30, 2016.

(51) Int. Cl.
*G16H 10/60*     (2018.01)
*G06Q 50/22*     (2018.01)
(Continued)

(52) U.S. Cl.
CPC ..... *G16H 10/60* (2018.01); *G06Q 10/063112* (2013.01); *G06Q 50/22* (2013.01); *G16H 15/00* (2018.01); *G16H 50/30* (2018.01)

(58) Field of Classification Search
CPC .................................................. G16H 10/60
See application file for complete search history.

(56) References Cited

U.S. PATENT DOCUMENTS 11,043,143 B2 *   6/2021   Ratcliffe ................. G09B 5/00
2006/0184407 A1     8/2006   Ozaki et al.
(Continued)

FOREIGN PATENT DOCUMENTS

CN     204043615 U   *   12/2014
EP       1 691 313 A2      8/2006
(Continued)

OTHER PUBLICATIONS

Philips Healthcare—Medical Equipment—Deals and Alliances Profile. London: GlobalData plc, 2016. (Year: 2016).*
(Continued)

*Primary Examiner* — Sheetal R Paulson
(74) *Attorney, Agent, or Firm* — Scully, Scott, Murphy & Presser, P.C.

(57) ABSTRACT

A medical-information providing system includes an electronic medical record system configured to accumulate medical-record information about patients; a medical device system configured to accumulate operation logs of medical devices; and a computer configured to provide medical-activity-related information from the medical-record information and the operation logs. The computer includes at least one processor configured to: acquire the medical-record information from the electronic medical record system; calculate a first parameter of a first medical activity corresponding to the acquired medical-record information on the basis of the acquired medical-record information; acquire the operation logs from the medical device system; calculate a second parameter of the medical devices used in the first medical activity on the basis of the acquired operation logs; identify a second medical activity involving parameters similar to the calculated first and second parameters; and generate the medical-activity-related information on the basis of the identified second medical activity.

3 Claims, 16 Drawing Sheets

(51) Int. Cl.
  *G16H 15/00* (2018.01)
  *G16H 50/30* (2018.01)
  *G06Q 10/06* (2012.01)

(56) References Cited

U.S. PATENT DOCUMENTS

| | | | |
|---|---|---|---|
| 2008/0058612 A1 | 3/2008 | Ohyu et al. | |
| 2009/0326336 A1* | 12/2009 | Lemke | G16H 50/70 600/300 |
| 2011/0099032 A1* | 4/2011 | Miyasa | G16H 50/70 705/3 |
| 2012/0117088 A1 | 5/2012 | Kawakami et al. | |
| 2012/0189996 A1 | 7/2012 | Hager et al. | |
| 2014/0278558 A1 | 9/2014 | Utsunomiya et al. | |
| 2014/0287393 A1* | 9/2014 | Kumar | A61B 34/35 434/262 |
| 2016/0092821 A1 | 3/2016 | Ozaki et al. | |
| 2016/0098933 A1 | 4/2016 | Reiley et al. | |
| 2017/0221385 A1 | 8/2017 | Reiley et al. | |
| 2018/0253994 A1 | 9/2018 | Reiley et al. | |

FOREIGN PATENT DOCUMENTS

| | | |
|---|---|---|
| JP | 2004-355613 A | 12/2004 |
| JP | 2006-218236 A | 8/2006 |
| JP | 2006-218238 A | 8/2006 |
| JP | 2007-117637 A | 5/2007 |
| JP | 2008-086756 A | 4/2008 |
| JP | 2011-092286 A | 5/2011 |
| JP | 2011-141706 A | 7/2011 |
| JP | 4768567 B2 | 9/2011 |
| JP | 2012-521568 A | 9/2012 |
| JP | 2013-045263 A | 3/2013 |
| JP | 2013-239158 A | 11/2013 |
| JP | 2014-241173 A | 12/2014 |
| JP | 5780348 B1 | 9/2015 |
| WO | 2010/108128 A2 | 9/2010 |

OTHER PUBLICATIONS

International Search Report dated Oct. 4, 2016 issued in International Application No. PCT/JP2016/069453.

* cited by examiner

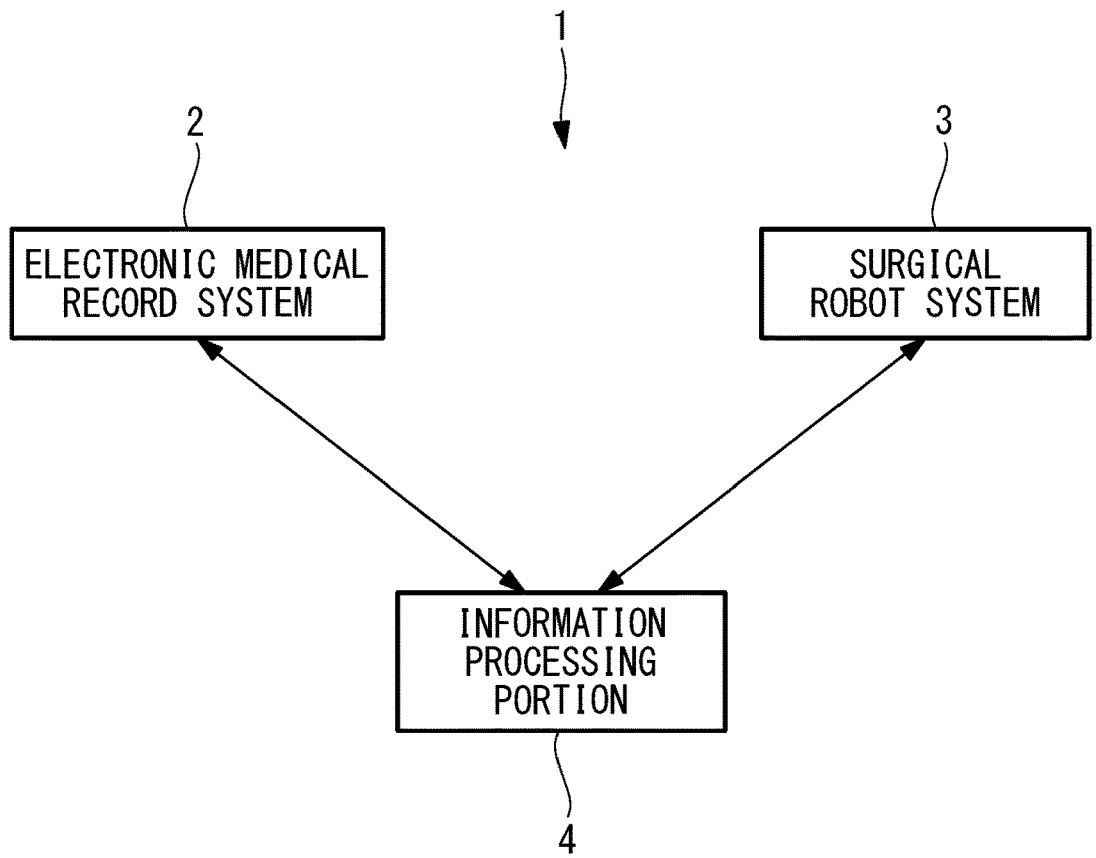

FIG. 3

| OPERATOR | TREATMENT TOOL | PROCEDURE CLASSIFICATION | MOVEMENT TRAJECTORY | REQUIRED AMOUNT OF TIME | MATTER TO BE NOTED |
|---|---|---|---|---|---|
| A | TREATMENT TOOL A1 | PROCEDURE P1 | | | |
| A | TREATMENT TOOL A2 | PROCEDURE P2 | | | |
| B | TREATMENT TOOL B1 | PROCEDURE P1 | | | |
| ⋮ | ⋮ | ⋮ | | | |

FIG. 5

| OPERATOR | PROCEDURE CLASSIFICATION | PATIENT INFORMATION | DIFFICULTY | CLINICAL SKILL | CLINICAL INFORMATION |
|---|---|---|---|---|---|
| A | PROCEDURE P1 | AGE 45<br>180cm<br>70kg<br>BMI<br>BLOOD PRESSURE<br>... | 80 | 74 | TYPE OF TREATMENT TOOL<br>POINTS TO BE NOTED |

FIG. 7

| OPERATOR | PROCEDURE CLASSIFICATION | PATIENT INFORMATION | DIFFICULTY | CLINICAL SKILL | CLINICAL INFORMATION |
|---|---|---|---|---|---|
| A | PROCEDURE P1 | 180cm 70kg ... | 80 | 74 | ... |
| A | PROCEDURE P2 | 170cm ... | 95 | 30 | ... |
| A | PROCEDURE P3 | 180cm ... | 75 | 68 | ... |
| A | PROCEDURE P4 | 160cm ... | 90 | 92 | ... |
| | | | | | |

FIG. 8

| OPERATOR | PROCEDURE CLASSIFICATION | PATIENT INFORMATION | DIFFICULTY | CLINICAL SKILL | CLINICAL INFORMATION |
|---|---|---|---|---|---|
| A | PROCEDURE P1 | 180cm 70kg ⋮ | 80 | 74 | |
| B | PROCEDURE P1 | 170cm ⋮ | 40 | 30 | |
| C | PROCEDURE P1 | 180cm ⋮ | 78 | 68 | |
| D | PROCEDURE P1 | 160cm ⋮ | 90 | 92 | |

FIG. 9

| OPERATOR | PROCEDURE CLASSIFICATION | PATIENT INFORMATION | DIFFICULTY | CLINICAL SKILL | CLINICAL INFORMATION |
|---|---|---|---|---|---|
| C | PROCEDURE P1 | 170cm 90kg ... | 78 | 68 | |
| C | PROCEDURE P2 | 170cm ... | 90 | 40 | |
| C | PROCEDURE P5 | 180cm ... | 72 | 98 | |
| C | PROCEDURE P6 | 160cm ... | 88 | 72 | |

FIG. 10

| OPERATOR | PROCEDURE CLASSIFICATION | PATIENT INFORMATION | DIFFICULTY | CLINICAL SKILL | CLINICAL INFORMATION |
|---|---|---|---|---|---|
| A | PROCEDURE P1 | 180cm 70kg ⋯ | 80 | 74 | |
| A | PROCEDURE P2 | 170cm ⋯ | 95 | 30 | |
| A | PROCEDURE P3 | 180cm ⋯ | 75 | 68 | |
| A | PROCEDURE P4 | 160cm ⋯ | 90 | 92 | |
| C | PROCEDURE P5 | 180cm ⋯ | 72 | 98 | |
| C | PROCEDURE P6 | 160cm ⋯ | 88 | 72 | |

FIG. 13

| OPERATOR | PROCEDURE CLASSIFICATION | PATIENT INFORMATION | DIFFICULTY | CLINICAL SKILL | CLINICAL INFORMATION |
|---|---|---|---|---|---|
| A | PROCEDURE P1 | 180cm 70kg ⋮ | 80 | 74 | |
| B | PROCEDURE P1 | 170cm ⋮ | 40 | 30 | |
| C | PROCEDURE P1 | 180cm ⋮ | 78 | 68 | |
| D | PROCEDURE P1 | 160cm ⋮ | 90 | 92 | |
| E | PROCEDURE P2 | 180cm ⋮ | 90 | 95 | |

FIG. 14

| OPERATOR | PROCEDURE CLASSIFICATION | PATIENT INFORMATION | DIFFICULTY | CLINICAL SKILL | CLINICAL INFORMATION |
|---|---|---|---|---|---|
| A | PROCEDURE P1 | 180cm 70kg ⋮ | 80 | 74 | |
| B | PROCEDURE P1 | 170cm ⋮ | 40 | 30 | |
| C | PROCEDURE P1 | 180cm ⋮ | 78 | 68 | |
| D | PROCEDURE P1 | 160cm ⋮ | 90 | 92 | |
| E | PROCEDURE P2 | 180cm ⋮ | 90 | 95 | |

FIG. 15

|  | 4/1 | 4/2 | 4/3 | ... | 5/7 | 5/8 | 5/9 | 5/10 |
|---|---|---|---|---|---|---|---|---|
| A | ○ | × | × | ... | × | × | ○ | ○ |
| B | ○ | ○ | ○ | ... | ○ | × | ○ | ○ |
| C | ○ | × | ○ | ... | × | ○ | ○ | ○ |
| D | × | ○ | ○ | ... | × | × | ○ | ○ |
| PATIENT | × | × | × | ... | ○ | ○ | ○ | × |
| HELPER | ○ | × | × | ... | ○ | ○ | ○ | × |
| OPERATING ROOM | ○ | ○ | × | ... | ○ | ○ | × | ○ |

FIG. 16

| OPERATOR | PROCEDURE CLASSIFICATION | PATIENT INFORMATION |||
|---|---|---|---|---|
| | | BIOLOGICAL INFORMATION | LESION INFORMATION | PROGNOSIS INFORMATION |
| A | PROCEDURE P1 | AGE 45<br>180cm<br>70kg<br>BMI<br>BLOOD PRESSURE<br>... | TYPE IIa<br>BACK SIDE OF FOLD<br>DIAMETER 3cm | HOSPITALIZED PERIOD<br>→10 DAYS<br>BLEEDING DURING AND AFTER SURGERY<br>→300mL<br>NUMBER OF NURSE CALLS MADE AFTER SURGERY<br>→4 |
| | | | | |

FIG. 17

| OPERATOR | PROCEDURE CLASSIFICATION | DIFFICULTY | CLINICAL SKILL | PROGNOSIS EVALUATION VALUE | CLINICAL EVALUATION VALUE |
|---|---|---|---|---|---|
| A | PROCEDURE P1 | 80 | 74 | 90 | 532800 | ns
MEDICAL-INFORMATION PROVIDING SYSTEM AND MEDICAL-INFORMATION PROVIDING METHOD

CROSS-REFERENCE TO RELATED APPLICATIONS

This is a continuation of International Application PCT/JP2016/069453 which is hereby incorporated by reference herein in its entirety.

TECHNICAL FIELD

The present invention relates to a medical-information providing system and a medical-information providing method.

BACKGROUND ART

There is a known method in which data related to surgical work performed by a user by using a surgical device are collected, and, by comparing the collected data and data about other similar surgical work, the clinical skill of the user is quantified and output (for example, see Patent Literature 1).

CITATION LIST

Patent Literature

{PTL 1} Japanese Translation of PCT International Application, Publication No. 2012-521568

SUMMARY OF INVENTION

An aspect of the present invention is a medical-information providing system including: an electronic medical record system configured to accumulate medical-record information about patients; a medical device system configured to accumulate operation logs of medical devices; and a computer configured to provide medical-activity-related information from the medical-record information and the operation logs, wherein the computer includes at least one processor, the at least one processor being configured to: acquire the medical-record information from the electronic medical record system; calculate a first parameter of a first medical activity corresponding to the acquired medical-record information on the basis of the acquired medical-record information; acquire the operation logs from the medical device system; calculate a second parameter of the medical devices used in the first medical activity on the basis of the acquired operation logs; identify a second medical activity involving parameters similar to the calculated first and second parameters; and generate the medical-activity-related information on the basis of the identified second medical activity.

In addition, another aspect of the present invention is an information processing device including: at least one processor, the processor being configured to: acquire medical-record information about patients from an electronic medical record system configured to accumulate the medical-record information; calculate a first parameter of a first medical activity corresponding to the acquired medical-record information on the basis of the acquired medical-record information; acquire operation logs of medical devices from a medical device system that accumulates the operation logs; calculate a second parameter of the medical devices used in the first medical activity on the basis of the acquired operation logs; identify a second medical activity involving parameters similar to the calculated first and second parameters; and generate medical-activity-related information on the basis of the identified second medical activity.

In addition, another aspect of the present invention is a medical-information providing method including: calculating a first parameter of a first medical activity on the basis of medical-record information about patients; calculating a second parameter of the medical devices on the basis of operation logs of medical devices used in the first medical activity; identifying a second medical activity involving parameters similar to the calculated first and second parameters; generating medical-activity-related information corresponding to the identified second medical activity; and outputting the generated medical-activity-related information.

BRIEF DESCRIPTION OF DRAWINGS

FIG. 1 is an overall configuration diagram showing a medical-information providing system according to an embodiment of the present invention.

FIG. 2 is a diagram showing an example of patient information accumulated in an electronic medical record system provided in the medical-information providing system in FIG. 1.

FIG. 3 is a diagram showing an example of operation-log information accumulated in a surgical robot system provided in the medical-information providing system in FIG. 1.

FIG. 5 is a diagram showing example data of a database provided in the information processing portion in FIG. 4.

FIG. 7 is a diagram showing example data identified in the database by using an operator A as the key.

FIG. 8 is a diagram showing example data identified in the database by using a procedure P1 as the key.

FIG. 9 is a diagram showing example data accumulated in the database regarding an operator C.

FIG. 10 is a diagram showing example data presented as procedures that can be executed by the operator A.

FIG. 13 is a diagram showing an example in which an operator E, who has a high clinical skill for the procedure P2 which is highly correlated with the procedure P1, is added as an operator who is capable of executing the procedure P1.

FIG. 14 is a diagram showing an example in which the information in FIG. 13 is selected on the basis of values of the clinical skills.

FIG. 15 is a diagram for explaining a case in which dates on which a surgery can be performed are presented on the basis of schedules accumulated in the electronic medical record system in FIG. 2.

FIG. 16 is a diagram showing a case in which prognosis information is included in the patient information accumulated in the electronic medical record system in FIG. 2.

FIG. 17 is a diagram showing example data of the database provided in the information processing portion in FIG. 4, including a prognosis evaluation value calculated on the basis of the prognosis information in FIG. 16 and a clinical evaluation value.

DESCRIPTION OF EMBODIMENT

A medical-information providing system 1 and a medical-information providing method according to an embodiment of the present invention will be described below with reference to the drawings.

As shown in FIG. 1, the medical-information providing system 1 according to this embodiment is provided with an electronic medical record system 2, a surgical robot system (medical device system) 3, and an information processing portion 4.

As shown in FIG. 2, the electronic medical record system 2 electronically accumulates patient information of a plurality of patients (medical-record information). The patient information includes biological information and lesion information.

The biological information includes age, sex, height, weight, body shape, blood pressure, past procedure history, presence/absence of complications, medical history of relatives, characteristics based on DNA analysis, etc. The lesion information includes classification result, position, size, etc. of a lesion.

As shown in FIG. 3, the surgical robot system 3 accumulates operating-log information generated while doctors (operators) operated medical devices in past procedures (medical activities) performed on the patients. The operation-log information includes identification information of the individual operators, information about used treatment tools, classifications of the procedures (medical activities) performed by using the treatment tools, movement trajectories of the treatment tools in the procedures, amounts of time required in individual steps of the procedures, information indicating matters to be noted when performing the procedures, etc.

Figure 4:
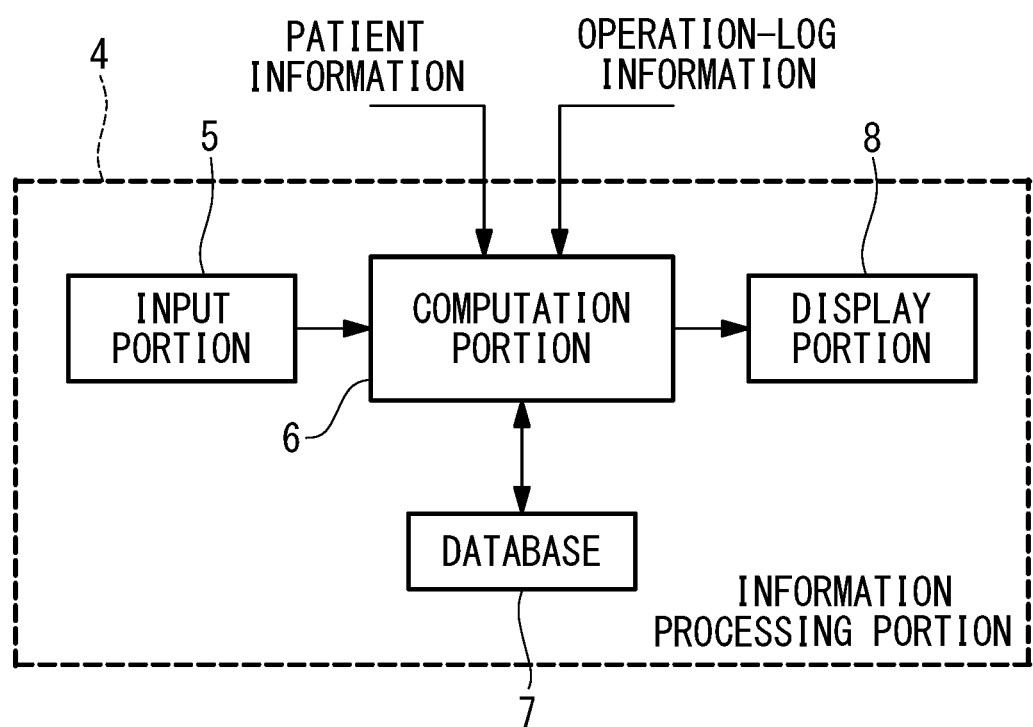
FIG. 4 is a block diagram showing an information processing portion provided in the medical-information providing system in FIG. 1.

As shown in FIG. 4, the information processing portion 4 is provided with: an input portion 5 used by a user for input; a computation portion 6 that performs computation on the basis of the patient information from the electronic medical record system 2 and the operation-log information from the surgical robot system 3; a database 7 in which computation results are accumulated; and a display portion 8 that displays, on the basis of the input to the input portion 5, data identified by the computation portion 6 from the data accumulated in the database 7.

The computation portion 6 calculates, on the basis of the patient information accumulated in the electronic medical record system 2, the difficulty of a procedure by using Eq. 1.

$$d = \alpha_0 + \Sigma_{n=1}^{k} f n(\alpha n) \quad \{Eq.1\}$$

where d is the difficulty,
$\alpha_0$ is the difficulty of the procedure,
$\alpha_n$ is the biological information or the lesion information,
k is the number of types of the biological information or the lesion information, and
$f_n(\alpha_n)$ is a function that indicates the relationship between the biological information or lesion information and the difficulty.

For example, $$f_n(\alpha_n) = a \times \alpha_n + b.$$

In addition, the computation portion 6 calculates, on the basis of the operation-log information accumulated in the surgical robot system 3, clinical skills required to perform the medical activities.

The clinical skills are calculated in a manner similar to that in Patent Literature 1.

In other words, because movements are better controlled with improved skills and it is possible to perform the treatment with a smaller amount of movement, values indicating greater clinical skills are calculated with a decrease in the total number of nodes in the movement trajectories of treatment tools accumulated in the operation-log information.

In addition, as shown in FIG. 5, the database 7 of the information processing portion 4 stores clinical information, such as the identification information of the operators, the classifications of the procedures, the patient information, the calculated difficulties, the calculated clinical skills, and points to be noted, etc., in association with each other.

Next, the accumulation of data performed by the medical-information providing system 1 according to this embodiment will be described.

First, as a result of an operator inputting the identification information of the operator, the classification of the planned procedure, and the patient information to the electronic medical record system 2, the electronic medical record system 2 issues a notification about the update of the patient information to the information processing portion 4.

The information processing portion 4 acquires, from the electronic medical record system 2, the patient information and the information about the classification of the planned procedure, and, in the computation portion 6, the difficulty of the procedure is calculated from the acquired information by using Eq. 1. As shown in FIG. 5, the calculated difficulty of the procedure is stored in the database 7 in association with the classification of the procedure and the patient information.

Then, when the registered operator actually performed the procedure by using the medical device, because the operation-log information generated when the medical device was operated in the procedure performed on the patient by the registered operator is accumulated in the surgical robot system 3, the information processing portion 4 receives the operation-log information from the surgical robot system 3 and calculates the clinical skill of the operator with respect to the procedure.

As shown in FIG. 5, the calculated clinical skill is stored in the database 7 in association with the identification information of the operator of the medical device, the classification of the procedure, the patient information, and the difficulty. In the case in which clinical information, such as the type of the utilized treatment tool, the information about the matters to be noted when performing the procedure, etc., is recorded in the operation-log information accumulated in the surgical robot system 3, this clinical information is also stored in the database 7 in association with the calculated clinical skill.

Next, the medical-information providing method employing the medical-information providing system 1 according to this embodiment will be described.

Figure 6:
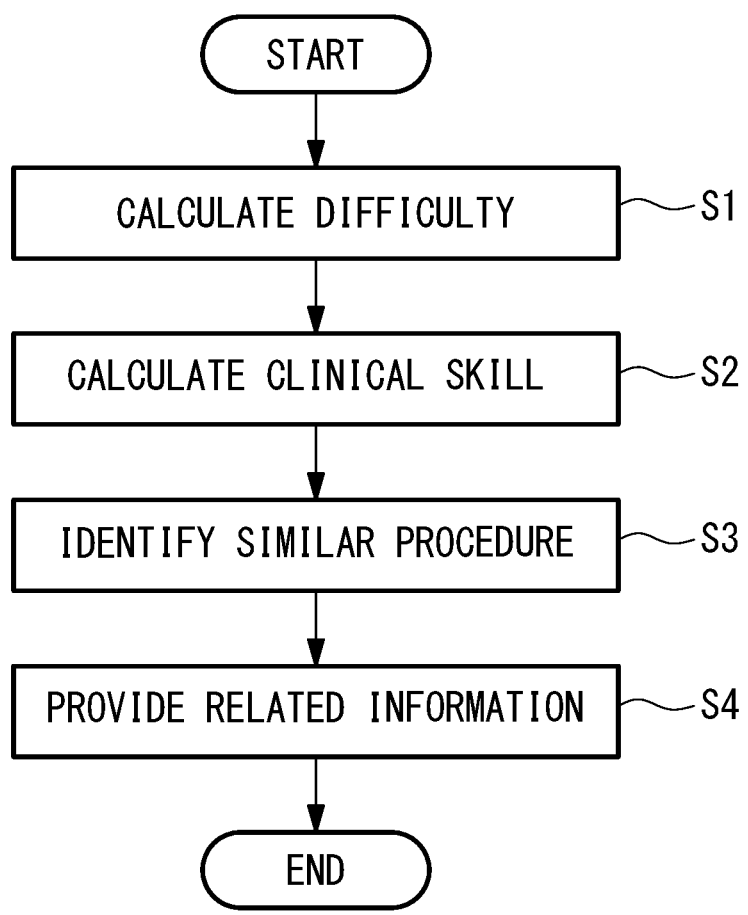
FIG. 6 is a flowchart for explaining a medical-information providing method based on the medical-information providing system in FIG. 1.

As shown in FIG. 6, the medical-information providing method according to this embodiment includes: a step S1 of calculating difficulties of past procedures for the individual patients on the basis of the medical-record information of the plurality of patients electronically accumulated in the electronic medical record system 2; a step S2 of calculating the clinical skills for medical devices required for the procedures on the basis of the operation-log information that is accumulated in the surgical robot system 3 and that is generated while operating the medical devices in the past procedures performed on the individual patients; a step 3 of identifying, on the basis of the calculated difficulties and clinical skills, the procedures performed in the past involving similar difficulties and clinical skills; and a step of providing related information associated with the identified procedures.

Specifically, when the operation-log information is accumulated in the surgical robot system 3 as a result of the patient information being input to the electronic medical record system 2 and any one of the operators performing a procedure employing the surgical robot system 3 on the patient, the step S1 of calculating the difficulties and the step 2 of calculating the clinical skills are performed, thus constructing the database 7.

In this state, as a result of an operator A himself/herself searching for an executable procedure by inputting his/her own identification information to the information processing portion 4, the operator A is provided with the information about the executable procedure, as well as related information associated with the procedure.

In this case, as a result of the operator A inputting his/her own identification information, the data stored in association with the identification information and data that are not associated with the identification information but satisfy certain conditions are read out. As shown in FIG. 7, the data stored in association with the identification information refer to data associated with the procedures that the operator A himself/herself has performed in the past.

Although the data that satisfy certain conditions are not stored in association with the identification information of the operator A because the operator A himself/herself has not performed the procedures in the past, the data includes information about the procedures that have been performed by other operators in the past, and the clinical skills thereof are approximated by those of other procedures of equivalent difficulties that both other operators and the operator A have performed in the past. The procedures to be selected may be assumed to be related procedures and may be registered in advance.

More specifically, as shown in FIG. 7, because the operator A has performed procedures P1, P2, P3, and P4 in the past, as a result of the operator A inputting his/her own identification information, the information about the procedure P1, P2, P3, and P4 stored in association with the identification information is read out, and the relationship with other operators with respect to the procedure P1 that the operator A has performed in the past is checked. In the example shown in FIG. 8, a search is performed on all the operators A to D with respect to the procedure P1, and the operator C who has a difficulty and a clinical skill that are similar to those of the operator A is identified. Here, the operator C is identified assuming that the difficulty and clinical skill of the operator C with respect to the procedure P1 are close to those of the operator A.

Here, the cases in which the difficulties are similar include cases in which a difficulty $Q_A$ of the procedure P1 performed by the operator A and a difficulty Q of the procedure P1 performed by the other operator B, C, or D have the relationship in expression (1) below:

$$Q_A \geq Q + \beta \qquad (1),$$

where $\beta$ is a real number that is equal to or greater than 0.

In addition, the cases in which the clinical skills are similar include cases in which a clinical skill $R_A$ of the procedure P1 performed by the operator A and a clinical skill R of the procedure P1 performed by the other operator B, C, or D have the relationship in expression (3) below:

$$R_A \geq R + \gamma \qquad (2),$$

where $\gamma$ is a real number that is equal to or greater than 0.

Also, as shown in FIG. 9, information about the procedures P5 and P6, which are registered as the information items related to the procedure P1, is queried from all past procedures for the operator C, and the procedures P5 and P6 with which the operator A has no experience but the operator C, who has similar difficulty and clinical skill with respect to the procedure P1, has experience, are also identified as the procedures the operator A can perform, thus being presented to the operator A who is the user, as shown in FIG. 10.

As has been described above, the medical-information providing system 1 and the medical-information providing method according to this embodiment not only quantitatively evaluate the clinical skills of the procedures the user performed in the past but are also based on the difficulties calculated on the basis of the patient information stored in the electronic medical record system 2 and the clinical skills calculated on the basis of the operation-log information stored in the surgical robot system 3; and therefore, it is possible to compare, by using the same scales, the difficulties and the clinical skills with respect to the procedures associated with other patients or other operators.

Therefore, there is an advantage in that it is possible to obtain useful information related to a new procedure to be performed before performing the procedure, and thus, it is possible to satisfactorily execute the procedure.

Note that, in this embodiment, as the useful information to be provided to the user, the information related to the procedures that are assumed for the user to be able to perform in the future is provided in addition to the information related to the procedures performed by the user in the past. In addition to this, procedure flows recommended by academic societies, academic papers, etc. may be stored, and, when the user has selected such a procedure, the procedure flow stored in association therewith may be presented as the useful information.

In addition, in the case in which equipment to be used in association with a procedure is determined in advance or in the case in which information indicating, for example, effective equipment for individual steps when the individual operators perform the procedure is recorded, when the user has selected the procedure, information, such as about the equipment stored in association therewith and the step in which this equipment should be use, etc. may be presented as the useful information.

In addition, in the case in which matters to be noted, such as steps in which bleeding tends to occur when the individual operators have performed the procedure, are recorded, when the user has selected the procedure, the matters to be noted stored in association therewith may be presented as the useful information.

In addition, the required amounts of time for the individual steps in the individual procedures may be stored, and, when the user has selected a procedure, the required amounts of time for separate steps stored in association therewith may be presented as the useful information.

In addition, in the above-described embodiment, although the operator C is selected assuming that the difficulty and the clinical skill are similar to those of the operator A, in the case in which the difficulties and the clinical skills of the procedure P1 have the relationships expressed by expressions (1) and (2), low negative real numbers β1 and γ1 may be set as β and γ.

Figure 11:
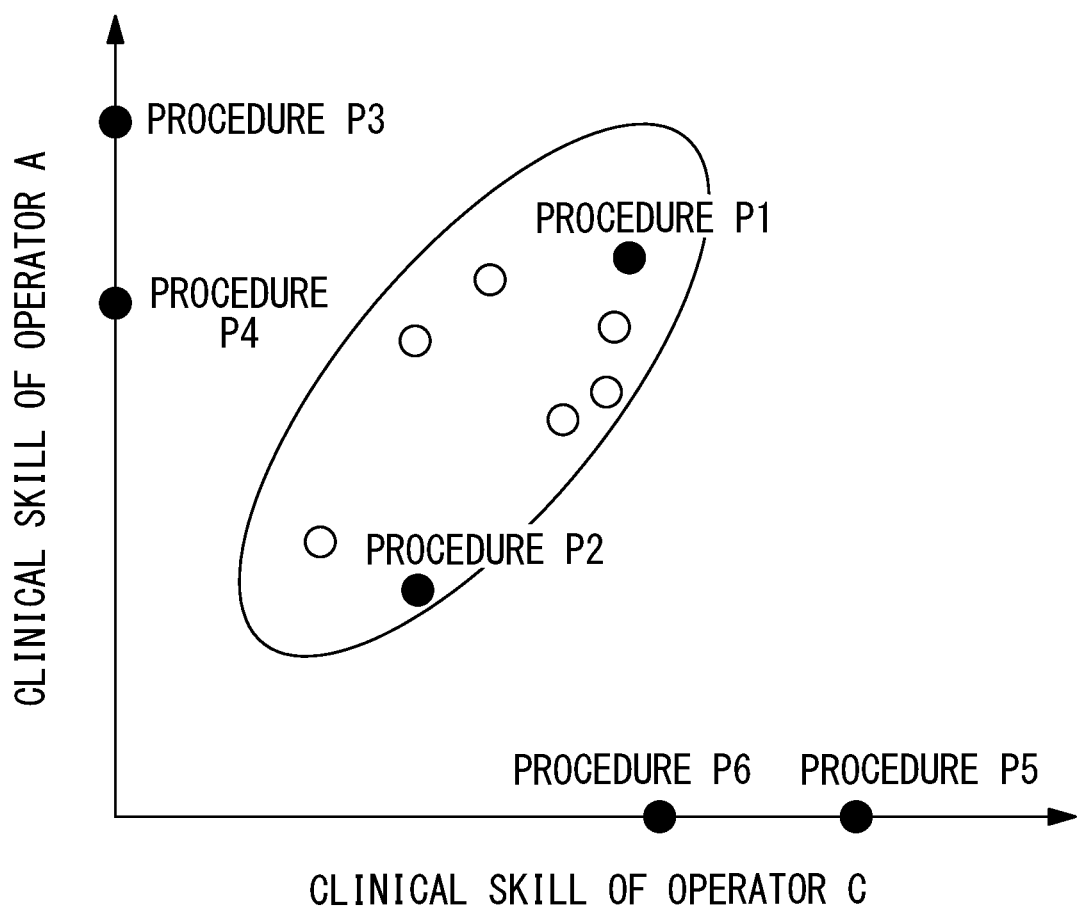
FIG. 11 is a diagram showing a correlation between clinical skills of the operator A and clinical skills of the operator C.

In addition, instead of selecting the operators by using expressions (1) and (2), the selectable operators may be determined on the basis of the presence/absence of a correlational relationship, as shown in FIG. 11.

For example, in the example shown in FIG. 11, by plotting the clinical skills of the different operators A and C by separately taking the operators A and C on the horizontal axis and the vertical axis, it is possible to obtain the distribution thereof, and it is possible to calculate a correlation coefficient r from this distribution by using the following expression.

In other words, when data rows consisting of two sets of values are given, the correlation coefficient r indicating the correlational relationship therebetween is expressed by expression (3) below:

$$r = S_{xy}/(S_x \cdot S_y) \qquad (3).$$

where $S_{xy}$ is the covariance, and $S_x$ and $S_y$ are standard deviations.

Therefore, in the case in which the correlation coefficient r of the clinical skill is, for example, equal to or greater than 0.8, the correlation can be determined to be high.

Similarly, the correlation coefficient may also be computed for the difficulty, and the past procedures P5 and P6 of another operator C may be identified, for whom the correlations with the operator A in terms of the difficulty and the clinical skill with respect to the procedure P1 are determined to be high.

In addition, the procedures P5 and P6 may be identified by calculating the relationship between the difficulty and the clinical skill by utilizing results other than the correlation coefficient that are calculated by general classification methods, such as classification methods such as SVM or the like, classification methods employing regression analysis or machine learning, and other statistical classification methods, etc or feature-quantity extraction methods.

Furthermore, procedures having similar operation flows may be identified from the operation data.

In addition, although this embodiment has been described in terms of the case of obtaining the effective information about the procedures executable by the operator A himself/herself and the effective information related to those procedures, there is no limitation thereto.

For example, by inputting a patient and procedures, a list of operators who can perform the procedures on the patient may be presented.

In this case, the information processing portion 4 calculates the correlational relationship between different procedures on the basis of the data of the plurality of operators by using Eq. 2 below:

$$r = \alpha_0 + \Sigma_{n=1}^{k} fn(\alpha n) \qquad \{\text{Eq. 2}\}$$

where r is the correlation coefficient between the procedures, $\alpha_0$ is the degree of correlation determined in advance, $\alpha_n$ is the operation-information feature quantity (for example, operation data) of the individual steps in the operation flow, k is the number of steps, and $f_n(\alpha_n)$ is a function for calculating the degree of correlation on the basis of the operation-information feature quantity.

Figure 12:
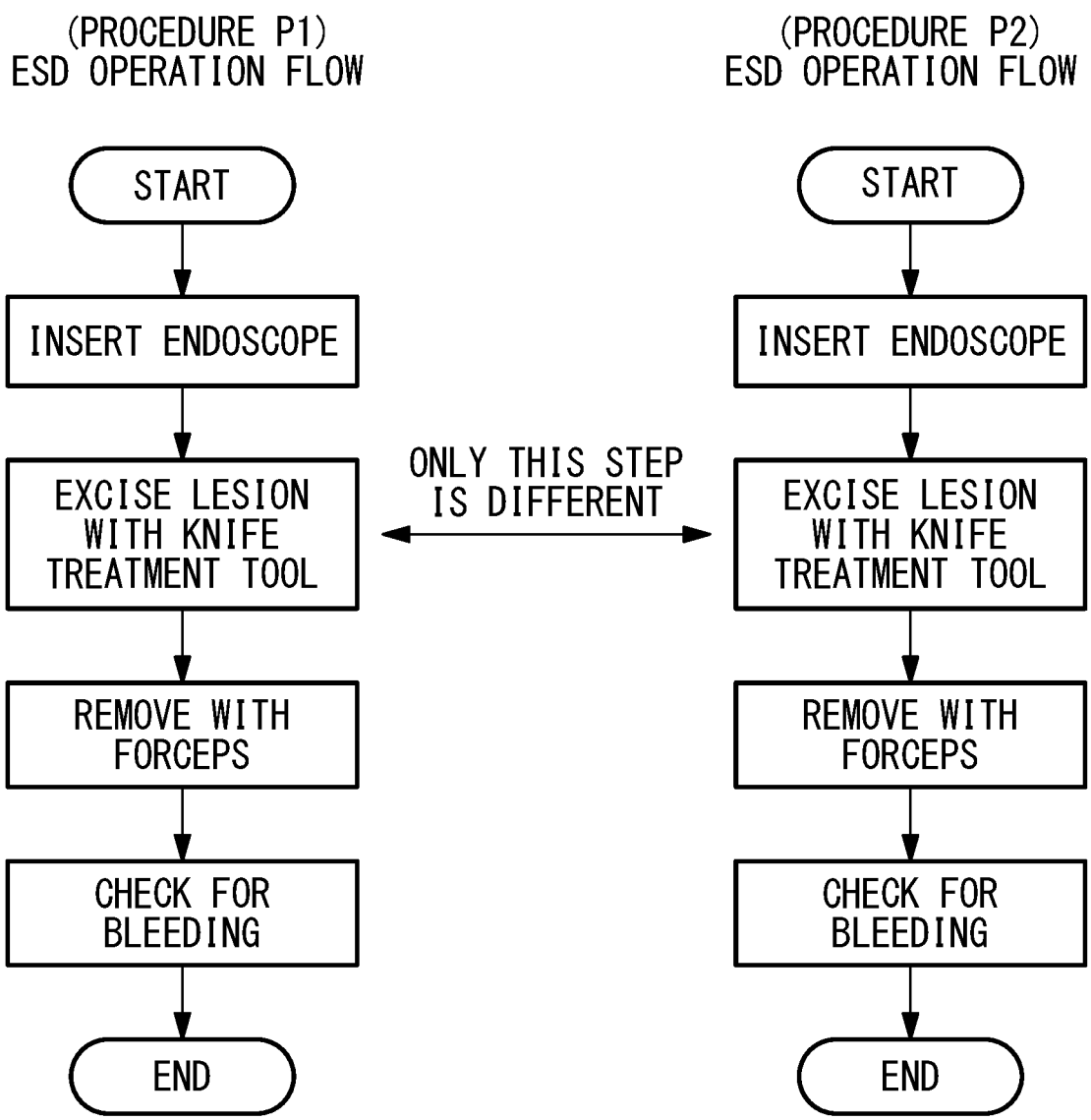
FIG. 12 is a diagram for explaining the presence/absence of a correlation between procedures based on a comparison between an operation flow of the procedure P1 and an operation flow of a procedure P2.

The information processing portion 4 may recognize operation flows, such as those shown in FIG. 12, on the basis of the operation data, and may determine whether or not the procedures are similar or not by detecting the difference therebetween. In the example shown in FIG. 12, operation flows of ESD (Endoscopic Submucosal Dissection) and EMR (Endoscopic Mucosal Resection) are compared, and, because the second steps differ from each other and other steps are the same, a high value is calculated as the degree of correlation.

The information processing portion 4 stores different procedures that are determined to have correlational relationships (for example, r>0.8). Then, in the case in which a surgery plan is input to the electronic medical record system 2, the information processing portion 4 searches for, by using the procedure information as the key, operators who can execute the input procedure, including the information related to the procedures having a correlational relationship therewith.

For example, as shown in FIG. 13, as a result of inputting the procedure P1, the operators A, B, C, and D who have performed the procedure P1 in the past are presented, and an operator E who has a high clinical skill for a procedure P2 that has a high correlational relationship with the procedure P1 is also presented.

In addition, in this embodiment, the list of the identified operators may be presented after filtering the data according to a predetermined condition. For example, as shown in FIG. 14, the operators to be presented may be selected on the basis of the values of the clinical skill. In the example shown in FIG. 14, the operator B whose clinical skill is lower as compared with those of the others is excluded from the information to be presented.

In addition, a scheduled surgery date may be adjusted on the basis of the patient's schedule, the operators' schedules, the helper's schedule, the information about the availability of the operating room, etc. input to the medical record, and the operators who can handle the surgery may be presented, as shown in FIG. 15. In the example shown in FIG. 15, the operator B is presented as being available to perform the surgery on May 7, and the operator C is presented as being available to perform the surgery on May 8.

In addition, the identified operators may be sorted by the values of their clinical skills, and the operators may be presented in a descending order of the clinical skills. Alternatively, a histogram may be created so that it is possible to compare the degrees of clinical skills of the individual operators.

In addition, in this embodiment, the electronic medical record system 2 may accumulate, as the patient information, prognosis information indicating the progress state after the procedure, as shown in FIG. 16; the information processing portion 4 may calculate a prognosis evaluation value indicating whether or not the prognostic progress is good on the basis of the prognosis information stored in the electronic medical record system 2 by using Eq. 3; and the information to be presented may be selected or updated on the basis of the prognosis evaluation values stored in the information processing portion 4 of the database 7, as shown in FIG. 17.

$$e = \Sigma_{n=1}^{k} fn(\alpha n) \qquad \{\text{Eq. 3}\}$$

where e is the prognosis evaluation value, $\alpha_n$ is the prognosis information, k is the number of types of the prognosis information, and $f_n(\alpha_n)$ is a function for calculating the evaluation value on the basis of the prognosis information.

Also, a clinical evaluation value $E_{total}$ may be calculated by multiplying the prognosis evaluation value calculated on the basis of the prognosis information, the difficulty, and the clinical skill by using expression (4) below, and ranking may be determined in a descending order of the clinical evaluation values:

$$E_{total} = d \times t \times e \qquad (4),$$

where d is the difficulty, t is the clinical skill, and e is the prognosis evaluation value.

In addition, it may be made possible to check what kind of treatment is performed when the clinical evaluation value is high. For example, clinical information such as the types of the employed treatment tools or the like may be stored in the electronic medical record system 2 in association with the operators, and, and when an operator is selected, the clinical information stored in association therewith may be presented. In addition, in the case in which the information stored in association is the operation flows of the procedures, the treatment tools utilized in the respective steps may be displayed.

In addition, as the clinical evaluation value, a result of a simple basic arithmetic operation, involving multiplication of the difficulty and the clinical skill, addition thereof, or multiplication by a coefficient, may be employed.

In addition, motions, treatment tools, and other information that are correlated with high clinical evaluation values may be identified by comparing, on the basis of data showing high clinical evaluation values, the clinical skill information and the other operation-log information, and the operator may be notified about the identified information when performing predetermined motions. By doing so, it is possible to enhance the clinical skill of the operator by using the motions that are quantitatively determined on the basis of high clinical evaluation values.

Alternatively, motions, treatment tools, and other information that are correlated with high clinical evaluation values may be identified by comparing, on the basis of data showing high clinical evaluation values, the clinical skill information and the other operation-log information, and this information may be used to update the related information. Also, once the information correlated with high clinical evaluation values are identified, such indicators may be used to perform further updates of the evaluation values of the difficulty and the clinical skill.

In addition, in this embodiment, although the procedures utilizing the surgical robot system 3 have been described as examples of medical activities, there is no limitation thereto, and other medical device systems for performing other medical activities, such as observation or the like, may be employed.

The above-described embodiment also leads to the following invention.

An aspect of the present invention is a medical-information providing system including: an electronic medical record system that electronically accumulates medical-record information about a plurality of patients; a medical device system that accumulates operation-log information generated when operating medical devices in medical activities performed in the past on at least one of the patients; and an information processing portion that calculates, on the basis of the medical-record information accumulated in the electronic medical record system, difficulties of the medical activities performed in the past, that also calculates, on the basis of the operation-log information accumulated in the medical device system, clinical skills with respect to the medical devices required in the medical activities performed in the past, that identifies, on the basis of the calculated difficulties and clinical skills, the medical activities performed in the past involving similar difficulties and clinical skills, and that provides medical-activity-related information corresponding to the identified medical activities.

With this aspect, the information processing portion calculates, on the basis of the medical-record information of the individual patients registered in the electronic medical record system, the difficulties of the medical activities performed in the past, and the information processing portion calculates, on the basis of the operation-log information accumulated in the medical device system for the individual operators, the clinical skills required for the medical activities performed in the past. Regarding the medical activities involving similar difficulties and requiring similar clinical skills, it may be possible to refer to each other among these medical activities even if the patients, the operators, or the classifications of the medical activities are different, and the information processing portion identifies the medical activities performed in the past involving similar difficulties and clinical skills, and provides the medical-activity-related information corresponding to the identified medical activities.

By doing so, it is possible to compare the medical activities corresponding to other patients or operators on the same scale by using the difficulties and the clinical skills, which has relatively been difficult in the related art due to individual differences of patients or operators. Therefore, it is possible to obtain useful information related to a new medical activity to be performed before performing the medical activity, and thus, it is possible to satisfactorily execute the medical activity.

In the above-described aspect, the operation-log information may be accumulated in association with operators of the medical devices, and the information processing portion may identify the operators of the medical devices suitable for the medical activities from the medical device system, and may present this information as the medical-activity-related information.

By doing so, the information about the operators of the medical devices suitable for the medical activities to be performed on specific patients is provided, and thus, it is possible to know, in advance, the effective information indicating that the operators who have performed satisfactory treatments in the past medical activities would perform equivalently satisfactory treatments.

In addition, in the above-described aspect, the operation-log information may be accumulated in association with classifications of the medical devices, and the information processing portion may identify the classifications of the medical devices suitable for the medical activities from the medical device system, and may present this information as the medical-activity-related information.

By doing so, the information about the classifications of the medical devices suitable for the medical activities to be performed on the patients is provided, and thus, it is possible to know, in advance, the effective information indicating that utilizing the classifications of the medical devices with which satisfactory treatments were performed in the past medical activities would result in equivalently satisfactory treatments.

In addition, in the above-described aspect, the operation-log information may be accumulated in association with operation flows of the medical activities performed in the past by using the medical devices, and the information processing portion may identify the operation flows from the medical device system, and may present this information as the medical-activity-related information.

By doing so, the operation flows of the medical activities to be performed on the patients are provided, and thus, even in the case in which the operators performing the treatment are inexperienced, it is possible to satisfactorily execute the medical activities by following the provided operation flows.

In addition, in the above-described aspect, the operation flows may include multiple steps, and may also include required amounts of time corresponding to individual steps, and the information processing portion may identify the required amounts of time corresponding to the individual steps of the operation flows from the medical device system, and may present this information as the medical-activity-related information.

By doing so, even in the case in which the operators performing the treatment are inexperienced, it is possible to satisfactorily execute the medical activities by referring to the required amounts of time of the individual steps in the operation flows when satisfactory treatments were performed in the past medical activities.

In addition, in the above-described aspect, the operation flows may include multiple steps and may also include information about matters to be noted, corresponding to the individual steps, and the information processing portion may identify the information about the matters to be noted, corresponding to the individual steps of the operation flows from the medical device system, and may present this information as the medical-activity-related information.

By doing so, the information about the matters to be noted, corresponding to the individual steps of the operation flows of the medical activities to be performed on the patients, is provided, and thus, even in the case in which the operators performing the treatment are inexperienced, it is possible to satisfactorily execute the medical activities by referring to the provided information about the matters to be noted.

In addition, in the above-described aspect, the electronic medical record system may accumulate, in association with the patients and the medical activities, prognosis information that indicates progress states after performing the medical activities, and the information processing portion may calculate, on the basis of the prognosis information, a prognosis evaluation value that indicates whether or not the prognostic progress is good, and may select or update, on the basis of the prognosis evaluation value, the medical-activity-related information to be provided.

By doing so, from among the medical activities performed in the past involving similar difficulties and similar required clinical skills, the medical-activity-related information related to the medical activities having satisfactory prognosis evaluation values is selected or updated. By doing so, it is possible to provide more effective information that is narrowed down with respect to the medical activities.

In addition, another aspect of the present invention is a medical-information providing method including: a step of calculating, on the basis of medical-record information about a plurality of patients, which is electronically accumulated in an electronic medical record system, difficulties of medical activities performed in the past on the individual patients; a step of calculating, on the basis of operation-log information that is generated when operating medical devices in medical activities performed in the past on the individual patients and that is accumulated in the medical device system, clinical skills with respect to the medical devices required in the medical activities; a step of identifying, on the basis of the calculated difficulties and required clinical skills, medical activities performed in the past involving similar difficulties and clinical skills; and a step of providing medical-activity-related information corresponding to the identified medical activities.

In the above-described aspect, the operation-log information may be accumulated in association with operation flows of the medical activities performed in the past by using the medical devices, and the medical-information providing method may include a step of identifying the operation flows from the medical device system and providing this information as the medical-activity-related information.

In addition, in the above-described aspect, the operation flows may include multiple steps and may also include required amounts of time corresponding to the individual steps, and the medical-information providing method may include a step of identifying the required amounts of time corresponding to the individual steps in the operation flows from the medical device system and providing this information as the medical-activity-related information.

In addition, in the above-described aspect, the operation flows may include multiple steps and may also include information about matters to be noted, corresponding to the individual steps, and the medical-information providing method may include a step of identifying the information about the matters to be noted, corresponding to the individual steps of the operation flows, from the medical device system and providing this information as the medical-activity-related information.

In addition, in the above-described aspect, the electronic medical record system may accumulate, in association with the patients and the medical activities, prognosis information that indicates progress states after performing the medical activities, and the medical-information providing method may include a step of calculating, on the basis of the prognosis information, a prognosis evaluation value that indicates whether or not the prognostic progress is good, and selecting or updating, on the basis of the prognosis evaluation value, the medical-activity-related information to be provided.

REFERENCE SIGNS LIST 1 medical-information providing system
2 electronic medical record system
3 surgical robot system (medical device system)
4 information processing portion

The invention claimed is:
1. A medical-information providing system comprising:
an electronic medical record system configured to accumulate medical-record information about patients comprising:
identification information of a first operator of a surgical robot system comprising one or more treatment tools, wherein the one or more treatment tools is configured to be controlled to move along one or more movement trajectories of one or more nodes of the one or more treatment tools;
a procedure of a first classification performed by the first operator on a first patient;
biological information or lesion information of the first patient;
identification information of a second operator of the surgical robot system;
a procedure of a second classification performed by the second operator on a second patient; and
biological information or lesion information of the second patient;
a medical device system configured to accumulate operation logs of medical devices comprising:
a first total number of nodes in a first movement trajectory or trajectories of the one or more treatment tools recorded during performance of the procedure of the first classification performed by the first operator on the first patient; and a second total number of nodes in a second movement trajectory or trajectories of the one or more treatment tools recorded during performance of the procedure of the second classification performed by the second operator on the second patient; and a computer configured to provide medical-activity-related information from the medical-record information and the operation logs, wherein the computer comprises at least one processor, the at least one processor being configured to:

acquire the medical-record information from the electronic medical record system;

calculate a first parameter of a first medical activity corresponding to the acquired medical-record information on the basis of the acquired medical-record information, wherein calculating the first parameter comprises:

retrieve a first predetermined difficulty value of the procedure of the first classification from a storage;

retrieve a second predetermined difficulty value of the procedure of the second classification from the storage;

determine a first difficulty of the procedure of the first classification performed by the first operator on the first patient based on a first equation that combines the first predetermined difficulty value of the procedure of the first classification with a first relationship value that indicates a relationship between the biological information or lesion information of the first patient and the first difficulty; and determine a second difficulty of the procedure of the second classification performed by the second operator on the second patient based on the first equation that combines the second predetermined difficulty value of the procedure of the second classification with a second relationship value that indicates a relationship between the biological information or lesion information of the second patient and the second difficulty;

acquire the operation logs from the medical device system;

calculate a second parameter of the medical devices used in the first medical activity on the basis of the acquired operation logs, wherein calculating the second parameter comprises:

determine a first clinical skill of the first operator in performing the procedure of the first classification based on the first total number of nodes in the first movement trajectory or trajectories on the one or more treatment tools recorded during performance of the procedure of the first classification, wherein a decrease in the first total number of nodes corresponds to an increase in the first clinical skill; and determine a second clinical skill of the second operator in performing the procedure of the second classification based on the second total number of nodes in the second movement trajectory or trajectories on the one or more treatment tools recorded during performance of the procedure of the second classification, wherein a decrease in the second total number of nodes corresponds to an increase in the second clinical skill;

identify a second medical activity involving parameters similar to the calculated first and second parameters, wherein identifying the second medical activity comprises:

determine whether the first difficulty is within a first predetermined range of the second difficulty;

determine whether the first clinical skill is within a second predetermined range of the second clinical skill; and in response to determining that the first difficulty is within the first predetermined range of the second difficulty and determining that the first clinical skill is within the second predetermined range of the second clinical skill, identify one or more of:

the procedure of the second classification as a next procedure to be performed by the first operator on the surgical robot system; and the second operator as a next operator to perform the procedure of the first classification on the surgical robot system; and generate the medical-activity-related information on the basis of the identified second medical activity present the medical-activity-related information.

2. The medical-information providing system according to claim 1, wherein the operation logs include classifications of the medical devices, the classification of the medical devices comprising:

a first treatment tool classification of the one or more treatment tools utilized in the procedure of the first classification; and a second treatment tool classification of the one or more treatment tools utilized in the procedure of the second classification, and wherein the computer, in generating the medical-activity-related information, is configured to, in response to identifying the second operator as the next operator to perform the procedure of the first classification on the surgical robot system, identify the first treatment tool classification of the one or more treatment tools for use by the second operator as the next operator to perform the procedure of the first classification on the surgical robot system.

3. The medical-information providing system according to claim 1, wherein the medical-record information comprises:

prognosis information of the first patient after the procedure of the first classification is performed by the first operator on the first patient, prognosis information of the second patient after the procedure of the second classification performed by the second operator on the second patient, and wherein the computer is configured to determine a first prognosis evaluation value based on the prognosis information of the first patient recorded in the first record, and wherein the computer, in generating the medical-activity-related information, is configured to determine a first clinical evaluation value based on the product on the first difficulty, the first clinical skill, and the first prognosis evaluation value;

determine a second prognosis evaluation value based on the prognosis information of the second patient recorded in the second record;

determine a second clinical evaluation value based on the product on the second difficulty, the second clinical skill, and the second prognosis evaluation value;

rank the first clinical evaluation value and the second clinical evaluation value in descending order; and in response to ranking the first clinical evaluation value as higher than the second clinical evaluation value, identify the first movement trajectories or trajectories on the one or more treatment tools.

* * * * *